United States Patent [19]

Johansson et al.

[11] Patent Number: 5,310,676
[45] Date of Patent: May 10, 1994

[54] CELL CULTIVATING DEVICE

[75] Inventors: Arne Johansson, Lejre; Peter Esser, Copenhagen, both of Denmark

[73] Assignee: A/S Nunc, Roskilde, Denmark

[21] Appl. No.: 978,624

[22] Filed: Nov. 19, 1992

Related U.S. Application Data

[63] Continuation-in-part of Ser. No. 804,085, Dec. 6, 1991, abandoned.

[30] Foreign Application Priority Data

Nov. 15, 1991 [EP] European Pat. Off. ........ 91610090.2
Oct. 7, 1992 [WO] PCT Int'l Appl. ................ PCT/DK92/00295

[51] Int. Cl.$^5$ ..................... C12M 3/04; C12M 1/24; C12M 1/14
[52] U.S. Cl. ................... 435/285; 435/296; 435/310
[58] Field of Search ............... 435/310, 296, 285, 300, 435/301

[56] References Cited

U.S. PATENT DOCUMENTS

| | | | |
|---|---|---|---|
| 3,870,602 | 3/1975 | Froman et al. | 195/139 |
| 4,172,013 | 10/1979 | Skoda et al. | 435/240 |
| 4,228,243 | 10/1980 | Lizuka | 435/285 |
| 4,334,028 | 6/1982 | Carver | 435/284 |
| 4,734,373 | 3/1988 | Bartal | 435/296 |
| 4,770,854 | 9/1988 | Lyman | 422/102 |
| 4,927,764 | 5/1990 | Lyman et al. | 435/296 |

FOREIGN PATENT DOCUMENTS 3413707 10/1985 Fed. Rep. of Germany .
841569 5/1939 France .
1539263 1/1979 United Kingdom .

*Primary Examiner*—Robert J. Warden
*Assistant Examiner*—E. Leigh Dawson
*Attorney, Agent, or Firm*—Klein & Szekeres

[57] ABSTRACT

A cell cultivating device comprising superposed, separate partition wall members forming mutually spaced partition walls, which define superposed chambers for containing a cell cultivating medium therebetween. The superposed partition wall members each comprising said partition wall and an upstanding peripheral wall extending transversely thereto, are arranged within a closed outer container having a flat bottom wall and a flat end wall. A liquid cultivating medium may be introduced into the outer container through a filling opening while the container is in an upright position in which it is supported by the end wall. The liquid may then substantially uniformly distribute itself within the cultivating chambers via a tunnel extending along the end wall and interconnecting the cultivating chambers. The partition wall members are preferably sealingly interconnected along the periphery thereof, and the free end of the upper partition wall member may be spaced from the inner surface of the container top wall in order to reduce problem of leakage of liquid medium between the chambers.

36 Claims, 3 Drawing Sheets

U.S. Patent May 10, 1994 Sheet 3 of 3 5,310,676
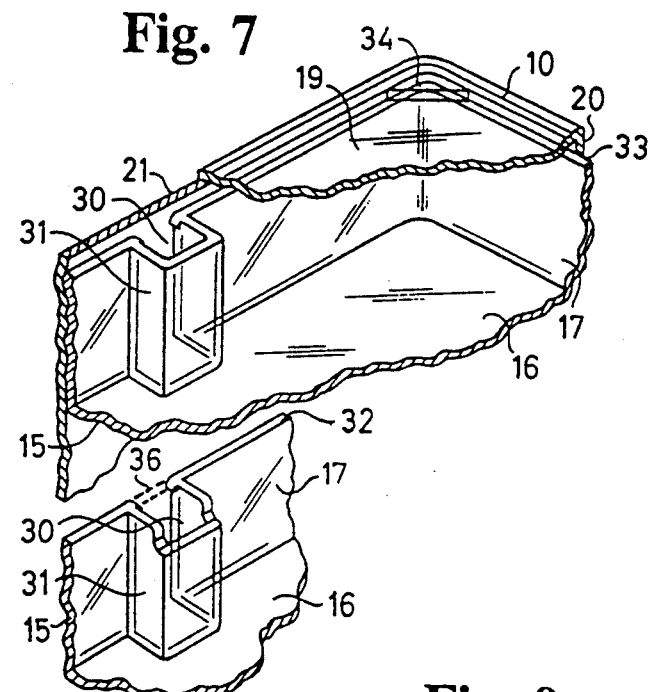
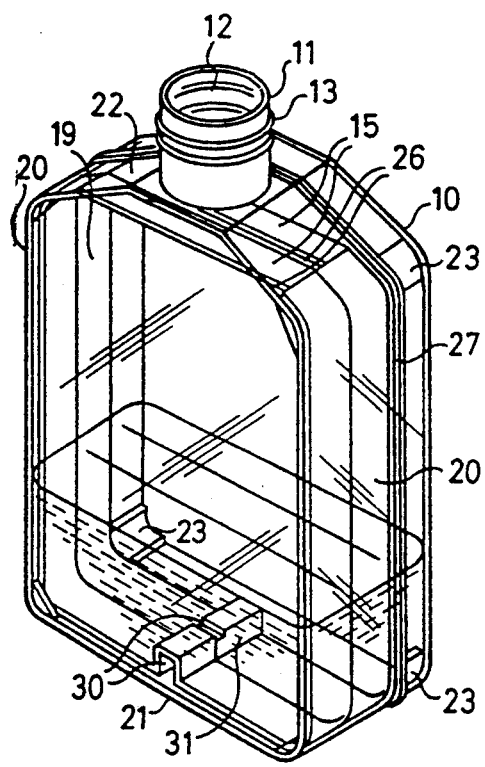
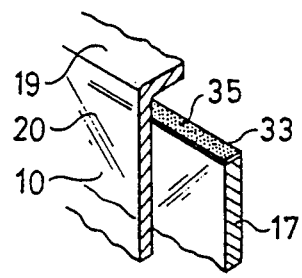
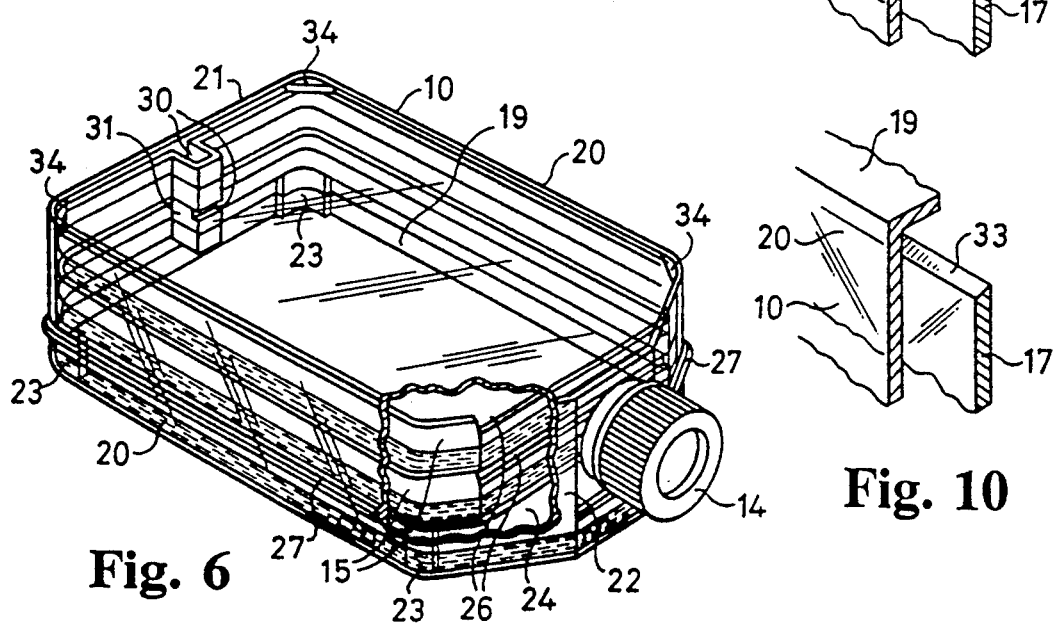
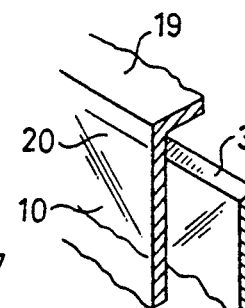

CELL CULTIVATING DEVICE

CROSS-REFERENCE TO RELATED APPLICATION

This application is a continuation-in-part of co-pending application Ser. No. 07/804,085; filed Dec. 6, 1991; now abandoned.

BACKGROUND OF THE INVENTION

1. Field of the Invention

The present invention relates to a cell cultivating device.

2. Description of Prior Art

Developments within cell biology have led to increased demands for devices for the production of eucariotic cells, with the purpose of producing biologically active compounds produced by the cells.

For static cultures it is well known to use a flat, flask- or bottle-like, closed container having a neck defining an opening which may be closed by means of a screw cap. When the container is in use it is arranged with a pair of spaced, parallel larger side walls in a substantially horizontal position, and a liquid cell cultivating medium covers the inner surface of the lower container wall, which may have been subject to a surface treatment allowing good cell attachment. As cell cultivation may take place only on the inner surface o the lower container wall or the bottom wall the production capacity of such a flask- or bottle-like container is rather limited.

U.S. Pat. No. 4,734,373 discloses a disposable cell culture device comprising a flask-like container with a neck defining an opening for introducing and removing cultivating medium and cells. The container contains a micro-constructed embodiment integrated in a unitary structure with the bottom wall of the container. The micro-embodiment comprises mutually spaced, interconnected plates having pores defined therein. When in use the micro-embodiment is submerged into a cultivating medium contained in the container. After use the cultivating medium may be discharged through the container neck, and the cells produced may be flushed out from the container in a known manner.

DK-B-143568 discloses an apparatus for mass cultivation of diploid cells, the apparatus being formed by a stack of superposed trays clamped together by means of bolts so as to define superposed closed cultivating chambers, which are interconnected by inlet passages. When a suitable total amount of cultivating medium has been filled into the apparatus through the inlet passages this medium may be distributed substantially evenly in the various chambers by placing the apparatus so that the chambers extend vertically, and subsequently moving the apparatus back to its normal position in which the chambers are horizontal. The upper surface of each tray may have been subject to a treatment securing improved cell attachment and growth.

The latter known cultivating device or apparatus may comprise any desired number of trays so that a large area covered with liquid cultivating medium may be obtained. However, care must be taken to ensure that adjacent trays are kept in sealing engagement with each other in order that cultivating medium from the cultivating chambers cannot leak out between the adjacent trays defining the respective chamber, and so as to prevent gas from escaping from and prevent atmospheric air from flowing into the cultivating chambers.

GB-A-1,539,263 discloses an apparatus for growing cells and comprising a plurality of cell attachment plates, which are arranged one above the other, and which are contained within a closed container having a filling or inlet opening for cell suspension. Each cell attachment plate, which is rectangular, is fused with the adjacent container walls along three sides. At one side each cell attachment plate is provided with an upstanding wall, which is spaced from the adjacent container wall.

In order to fill cell suspension into this known apparatus and have it distributed on the various cell attachment plates, the apparatus is placed in a filling position in which the apparatus is supported by one of the container side walls. Thereafter, the apparatus is tilted to a second position in which the apparatus is supported by another container side wall, and finally, the apparatus is tilted to a position of use in which the cell attachment plates extend horizontally and the apparatus is supported by the container bottom wall or by feet provided thereon.

SUMMARY OF THE INVENTION

The present invention provides an improved cell cultivating device which is more simple and convenient to use. Thus, the present invention provides a cell cultivating device comprising a container, which includes a substantially flat bottom wall, a top wall, a substantially flat first end wall extending at substantially right angles to the flat bottom wall, a second end wall, opposite side walls interconnecting the top and bottom walls and the end walls, one of said walls defining a closable filling opening therein, at least one flat partition wall member including a chamber bottom wall that extends substantially parallel with the flat container bottom wall, the partition wall member being arranged within an inner space of the container so as to divide the inner space into superposed cultivating chambers, and means for mutually interconnecting all of the superposed cultivating chambers so that liquid introduced into the container via the closable filling opening may distribute itself in all of the interconnected chambers when the container is placed in an upright position in which it is supported by the flat first end wall, said interconnecting means comprising an interconnecting passage defined at an inner side surface part of the flat first end wall, each chamber communicating with the interconnecting passage through a connecting opening extending along only a small fraction of the width of the first end wall and being spaced from the bottom wall of the respective cultivating chamber.

A cell suspension or a cultivating liquid may be introduced into the container through the filling opening while the cell cultivating device is in a position in which it is supported by the flat first end wall of the container. In this position the liquid introduced into the container may distribute itself in the various cultivating chambers which are mutually interconnected by the interconnecting passage. When the liquid has distributed itself within the chambers the cell cultivating device may immediately be turned into a position in which it is supported by the flat bottom wall of the container and in which the chamber bottom walls or cell attachment walls are substantially horizontal. As the connecting openings are relatively short no substantial amount of the liquid distributed in the cultivating chambers may flow from one chamber into another when the cell cultivating device is suddenly turned form its filling position into its position of use in which it is supported by the bottom wall of the container.

The edges of the flat chamber bottom walls or cell attachment walls may be fused or sealed with the adjacent side walls and end walls of the container. In the preferred embodiment, however, each partition wall member comprises a flat chamber bottom wall having a peripheral wall surrounding the chamber bottom wall and engaging with adjacent inner surface parts of the container walls, said peripheral wall extending from the chamber bottom wall towards the top wall of the container.

The liquid cultivating medium may be introduced into the superposed cultivating chambers so that the upper surface of each of the partition wall members and possibly also the inner surface of the bottom wall of the outer container may be covered by the liquid cell cultivating medium. This means that while the advantages of a closed container are maintained the cell cultivating area may be multiplied as desired by choosing a corresponding number of partition wall members.

The cell cultivating device according to the invention may be used for the production of various biological substances, such as viruses, vaccines, interferon, interleukin, hormones, antibodies, etc. Most cells used for the manufacture of the products mentioned above grow better and often only when attached to a suitable substratum. Therefore, at least part of the upper surfaces of the partition well members and possibly also of the inner surface of the bottom wall of the outer container may be treated in a manner which secures optimum cell attachment and growth.

The outer container and/or the partition wall members may be made from metal, glass or plastics, preferably from polystyrene.

The partition wall members may, for example, be supported by inwardly directed projections or shelves formed on the inner side surfaces of side walls of the outer container. In the preferred embodiment, however, each partition wall member is arranged on top of and supported by a free edge portion of the peripheral wall of an adjacent lower partition wall member. The lowermost partition wall member may then be supported, for example by adjacent wall parts of the outer container in spaced relationship with the bottom wall of the container so as to define a cultivating chamber between the lower partition wall member and the container bottom wall.

As mentioned above the partition wall members may be supported by projections formed on the inner surfaces of the side walls of the outer container, whereby the partition wall members may be mutually spaced as desired. However, the mutual spacing of the partition wall members may alternatively be obtained by spacing members or legs arranged on the bottom surface of the lowermost partition wall member and/or on the adjacent container wall. Such spacing members may, for example, be spacing members or ribs formed integrally with and extending from said container wall.

When the cultivating device comprises two or more partition wall members assembling of the various parts of the cultivating device is facilitated if the partition wall members are mutually interconnected, for example by spot welding, so as to form a unit which may in turn be attached to the inner surface of the outer container, if desired. Alternatively, the partition wall members may be removably or detachably arranged within the closed outer container and even in this case leakage of cultivating medium to the environment and gas flows into and out from the inner space of the cultivation device are effectively prevented.

It has been found that in practical use the cultivating medium, which has been poured into the cultivating device, tends to foam, and that the foaming medium arranged within the superposed cultivating chambers tends to leak through capillary spaces defined between the upstanding peripheral wall of a partition wall member and adjacent surface parts of the outer container and/or an adjacent partition wall member. Therefore, part of the foaming cultivating medium contained in an upper cultivating chamber tends to leak downwardly into an underlying chamber. In order to prevent or substantially reduce such leakage adjoining partition wall members may be sealingly interconnected along a major part of the periphery thereof and the non-interconnected part of the periphery of the adjoining partition wall members may be substantially spaced so as to define opening therebetween, namely the connecting openings formed in the interconnecting passage, and other openings interconnecting the filling opening of the outer container and the various cultivating chambers. Thus, the partition wall members of the cell-cultivating cultivating device may be heat-sealed, glued or otherwise sealingly interconnected along their periphery so as to form a unitary insert.

The outer container may be made from at least two separate parts, which may be sealingly interconnected when the partition wall members have been arranged within the container. Like the partition wall members the container parts may be interconnected, for example by gluing, heat sealing, ultra-sonic sealing or by any other suitable sealing method.

The liquid cell cultivating medium may be introduced into the cultivating device through the filling opening which may be sealingly closed by means of a closing member of any suitable type, such as a screw cap. The filling opening may in principle be formed in any of the top and bottom walls or side walls of the container. However, the closable filling opening is preferably formed in said second end wall of the container, and the liquid cultivating medium may then conveniently by poured into the container while it is supported by its flat first end wall, in which position the liquid poured into the container may distribute itself into the various cultivating chambers via the interconnecting passage.

The interconnecting passage may be a tunnel defined between an inner side surface part of the flat first end wall and an opposite outer surface part of the peripheral wall of each partition wall member. Such tunnel may be formed by a channel defined by inner surface parts of the flat container defined in a strengthening rib of the container end wall. Alternatively or additionally, the tunnel may be formed by a channel defined by said outer surface part of the peripheral wall.

The interconnecting passage or tunnel may have any cross-sectional shape, such as circular, semi-circular, or triangular shape. In the preferred embodiment, however, the interconnecting passage has a quadrangular, such as a trapezoidal or a rectangular (including a square), cross-sectional shape.

The tunnel—which may be defined by aligned channels formed in other surface parts of the peripheral walls of the superposed partition wall members and/or adjacent container end wall and arranged in end to end relationship—interconnects the various superposed cultivating chambers. Thus, the tunnel may have open ends positioned opposite to and spaced from the bottom and top walls, respectively, of the container, whereby the upper and lower cultivating chambers are interconnected. Each intermediate cultivating chamber may be connected with the tunnel via a connecting opening, which is defined in a tunnel wall part spaced from the inner surface part of the adjacent flat first end wall. Each connecting opening is preferably positioned adjacent to the partition wall forming a chamber top wall of the respective cultivating chamber.

When a liquid cultivating medium or cell suspension has been poured into the container while it is in its filling position and supported by its flat first end wall and the liquid has been allowed to distribute itself within the various chambers via the interconnecting passage, the cell cultivating device may be tilted directly to its position of use in which it is supported by the flat bottom wall of the container, and in which all of the substantially parallel partition walls extend substantially horizontally. As the end openings and the connecting openings of the tunnel or interconnecting passage are relatively small, only rather small amounts of liquid can escape from one cultivating chamber to another during such tilting movement. As an example, each connecting opening may extend along less than $\frac{1}{2}$ and preferably less than $\frac{1}{4}$ of the length of the first end wall of the container. As an example, the connecting opening may extend along only approximately 1/10 of the length of the first end wall, whereby the amount of liquid which may move from one chamber to another by tilting the cultivating device from its filling position to its position of use in which it is supported by the bottom wall of the container will be negligible.

As is it desirable to utilize the inner volume of the outer container of the cultivating device to the highest possible extent the peripheral wall of each partition wall member should preferably be in abutting engagement with the opposite container end walls and container side walls along at least the major part of the outline of the container. This means that no substantial amount of liquid can flow from one chamber to another through the space defined between the peripheral wall of the partition wall member and the adjacent inner wall surface of the container when the cell cultivating device is tilted from its filling position to its position of use.

As mentioned above, a cell cultivating medium or cell suspension poured into the cell cultivating device may tend to foam, and the foaming liquid may tend to leak from an upper to a lower cultivating chamber via the capillary space defined between the peripheral wall of each partition wall member and the adjacent inner wall surface of the container. In order to counteract such tendency of leakage from the upper partition wall member the free edge of the peripheral wall of the partition wall member positioned adjacent to the top wall of the container may be spaced from this top wall. Such spacing may, for example, be 1-2 mm or even more.

The leakage of liquid from the upper partition wall member may alternatively or additionally be counteracted by forming the free edge of the peripheral wall of the partition wall member positioned adjacent to the top wall of the container so that it defines a sharp edge. Alternatively or additionally, this free edge of the peripheral wall may be made hydrophobic, for example by applying a layer of hydrophobic material, such as silicone, to such free edge.

When cells have been cultivated within the cultivating device according to the invention they may be scraped from the partition wall members, for example by means of a scraping implement being inserted through the filling or liquid inlet opening formed in the container, or the cells may be flushed out in any conventional manner. It is also possible to cut a wall part from the container so that the partition wall members, which may be interconnected to a unit or mutually separate, may be removed from the outer container prior to scraping the cultivated cells from the partition wall members. Alternatively, the container may comprise a tear-off or peel-off wall part. Such tear-off wall part may, for example, be made from a metal foil or from a plastic film which has been fastened to the remaining part of the container, for example by heat sealing or gluing. In an alternative embodiment, however, the tear-off wall is defined by a score line or weakening line formed in a container wall.

The container may then be formed by an upwardly open container part comprising a bottom wall and peripheral walls extending upwardly therefrom and having an upper rim portion and by a flat tear-off wall part, for example made from metal foil or plastic film, forming the top wall of the container. When the partition wall members have been inserted into the upwardly open container part the tear-off part may be detachably sealed to the upper rim portion of the upwardly open container part in any suitable manner, such as by gluing or heat sealing. Alternatively, the tear-off wall part may form an end wall of the container.

The closable filling opening of the container may open into a manifold chamber defined within the container and communicating with at least one of the cultivating chambers via an inlet opening formed in at least one of the partition wall members.

The inlet opening may be overflow openings formed in the partition wall members, for example notches or cut-outs formed in the upper edge portions of the peripheral walls of the partition wall. Such notches or cut-outs may possibly extend substantially the total length of the respective peripheral wall. Provided that the liquid level in each partition wall member does not reach the overflow opening, the liquid cannot escape from the partition wall member through the inlet opening when the cell cultivating device is supported by the bottom wall of the container and is in its position of use.

The outer closed container may be of any suitable size and shape, and the separate partition wall members arranged therein may have a corresponding contour. As an example, the outer container may be a conventional tissue culture flask providing a relatively small cell growth area at the inner surface of the bottom wall of the flask, for example in the order of 25-175 $cm^2$. Such a flask may, for example, be provided with two or three partition wall members, whereby the growth area may be increased by a factor three or four, respectively.

According to a further aspect the present invention provides a cell cultivating device comprising a container, which includes a substantially flat bottom wall, a top wall, a substantially flat first end wall extending at substantially right angles to the flat bottom wall, a second end wall, opposite side walls interconnecting the top and bottom walls and the end walls, one of said walls defining a closable filling opening therein, at least two superposed partition wall members dividing an inner space of the container into cultivating chambers, each partition wall member having a flat partition wall and an encircling peripheral wall extending from the partition wall towards the top wall of the container and engaging with adjacent inner surface parts of the container walls, the partition walls, which are mutually spaced and spaced from the top and bottom walls, respectively, of the container extending substantially parallel with the bottom wall of the container, and adjoining partition wall members being sealingly interconnected along a major part of the periphery thereof, the partition wall members being spaced along remaining, non-interconnected parts of said periphery, and means for mutually interconnecting all of the cultivating chambers so that liquid introduced into the container via the closable filling opening may distribute itself in all on the interconnected chambers when the container is placed in an upright position in which it is supported by the flat first end wall.

BRIEF DESCRIPTION OF THE DRAWINGS

The invention will now be further described with reference to the drawings, wherein FIGS. 5 and 6 are perspective views showing a third embodiment of the cultivating device according to the invention, FIGS. 7 and 8 are detailed perspective views showing a passage for interconnecting superposed cultivating chambers and formed in an upper and lower partition wall member, respectively, and FIGS. 9 and 10 illustrate various embodiments of the upper edge portion of the partition wall members.

DETAILED DESCRIPTION OF THE INVENTION

Figure 1:
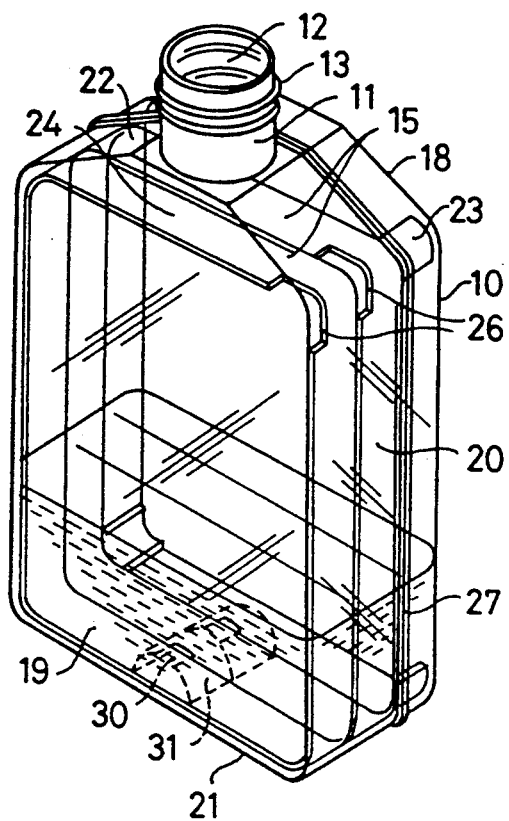
FIGS. 1 and 2 are perspective views of a first embodiment of the cultivating device according to the invention.
Figure 2:
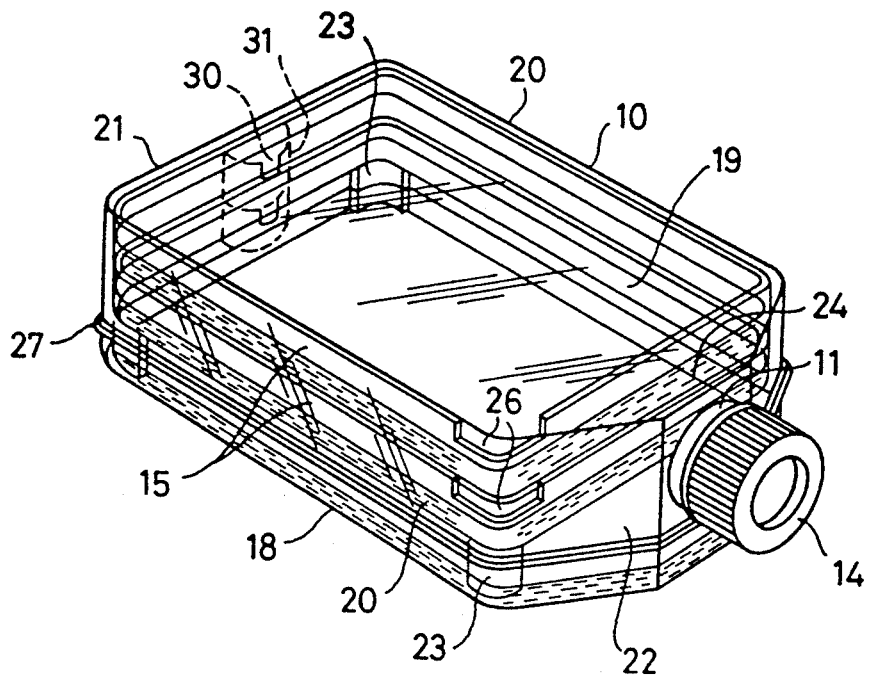

The cell cultivating device or apparatus shown in FIGS. 1 and 2 comprises an outer container or flask 10, which is made from a transparent or non-transparent material, such as glass or plastics material, or from metal. The container 10 is provided with a neck 11 defining a filling opening 12. The neck 11 is formed with outer screw threads 13 for cooperating with inner screw threads of a screw cap 14 by means of which the filling opening 12 may be closed. A number of partition wall members 15 having a bottom wall or cell attachment plate 16 and a surrounding peripheral side wall 17 (FIG. 4) extending upwardly therefrom, is arranged in superposed relationship within the container 10, so as to define cultivating chambers therein. The outer container 10 has a flat bottom wall 18, a top wall 19, opposite side walls 20, a flat end wall 21, and an opposite end wall 22 on which the neck 11 is formed.

The lower partition wall member arranged adjacent to the bottom wall 18 is supported by feet or spacer members 23 so that a cultivating chamber is defined between the inner surface of the container bottom wall 18 and the lower surface of the bottom wall 16 of the lower partition wall member 15. The spacer members 23 may be formed as integral parts of the walls of the outer container 10 or of the lower partition wall member. An upper cultivating chamber is defined between the inner surface of the container top wall 19 and the upper surface of the adjacent bottom wall 16 of the upper partition wall member 15. Furthermore, a cultivating chamber is defined between each pair of adjacent partition wall members 15. Thus, the embodiment shown in FIGS. 1 and 2 which comprises two partition wall members 15 defines three cultivating chambers therein.

The container end wall 22 has a convex contour so that a manifold chamber 24 is defined between the container end wall 22 and the adjacent side walls 17 of the partition wall members 15. Cut-outs in the peripheral side walls 17 of the partition wall members 15 define overflow openings 26 communicating with the manifold chamber 24.

The outer container 10 may be made from at least two separate container parts, which may, for example, be moulded from transparent plastics material. When the partition wall members 15 have been arranged within one of the container parts, such container parts may be sealingly interconnected, for example by interconnecting flanged rim portions of the container parts so as to form a heat seal 27 in a plane being substantially parallel with the bottom walls 16 of the partition wall members 15.

As indicated in broken lines in FIGS. 1 and 2 each of the partition wall members 15 further comprises an equalizing opening 30 formed in its peripheral side wall 17 adjacent to the container end wall 21. The equalizing opening 30 may be a cut-out formed in the rim portion of a curved part of the peripheral wall 17 of each partition wall member. The curved parts of the superposed partition wall members 15 define a transverse tunnel or passage 31 interconnecting the superposed cell cultivating chambers. The tunnel or passage 31 may have any suitable cross-sectional shape, which may, for example, be a semi-circle as shown.

When the cell cultivating device shown in FIGS. 1 and 2 is to be used it is positioned in its upright position shown in FIG. 1, and the screw closure cap 14 is removed. A suitable amount of cell cultivating medium and cells to be cultivated are poured into the manifold chamber 24 of the container 10 through the filling opening 12 defined by the neck 11. From the manifold chamber 24 of the liquid cultivating medium flows into one or more of the various cultivating chambers via the overflow opening 26 and through the opening defined between the inner surface of the container bottom wall 18 and the bottom wall 16 of the adjacent partition wall member 15. Now, as the cultivating chambers are all interconnected by the tunnel 31 and the openings 30 formed therein by the principle that liquid seeks its own level the liquid level within the cultivating chambers will be the same after a short period of time. Provided that the dimensions of the cultivating chambers are substantially the same, these chambers will now contain substantially the same amount of liquid.

When the filling opening 12 has been closed by means of the screw cap 14 the container or flask 10 may be a quick movement be tilted form the upright position shown in FIG. 1 to the position shown in FIG. 2 in which the container bottom wall 18 is supported in a substantially horizontal position. As the equalizing openings are relatively small, this simple procedure renders it possible to have substantially the same amount of liquid cultivating medium placed in all of the now horizontally extending cultivating chambers. This means that a layer of liquid cultivating medium containing cells to be cultivated is supported by the container bottom wall 18 and by the bottom walls or cell attachment plates 16 of each of the partition wall members 15. The surfaces of these walls have preferably been subject to a surface treatment allowing good cell attachment.

After expiration of the cultivating period the liquid cultivating medium may be poured out through the inlet opening 12 of the neck 11. Thereafter, the cells attached to the bottom walls 16 and 18 may be scraped or flushed out through the inlet or filling opening 12 in a manner known per se. Alternatively, the container bottom wall 18 or top wall 19, or any of the container side or end walls 20 and 21, respectively, may be cut away or otherwise removed so that the tray members may be taken out from the container 10, whereafter the cultivated cells may be scraped flushed from the bottom walls 16 and 18.

The embodiments shown in FIGS. 3-8 are modified embodiments of the embodiment shown in FIGS. 1 and 2, and similar parts have been provided with same reference numerals.

Figure 3:
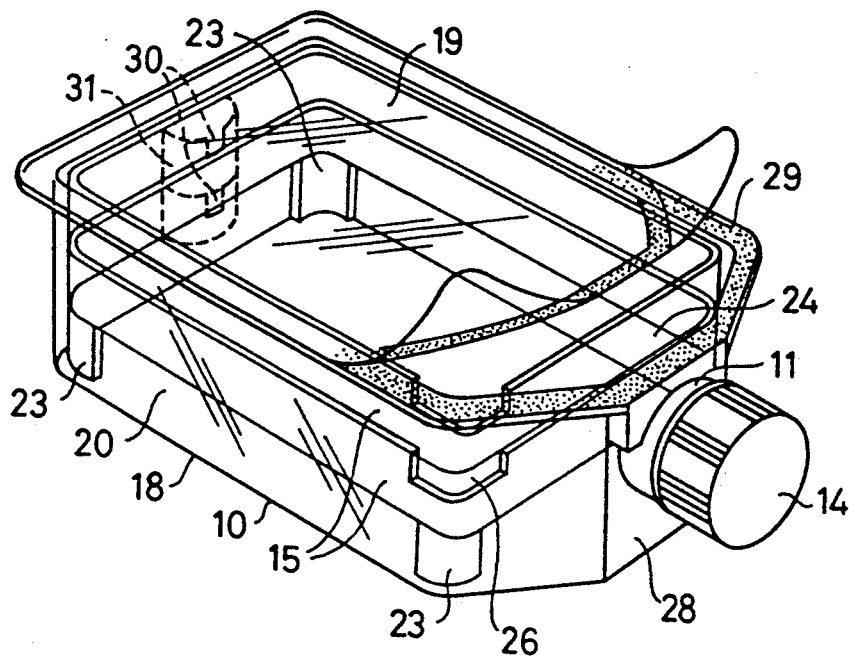
FIGS. 3 and 4 are perspective views of a second embodiment.
Figure 4:
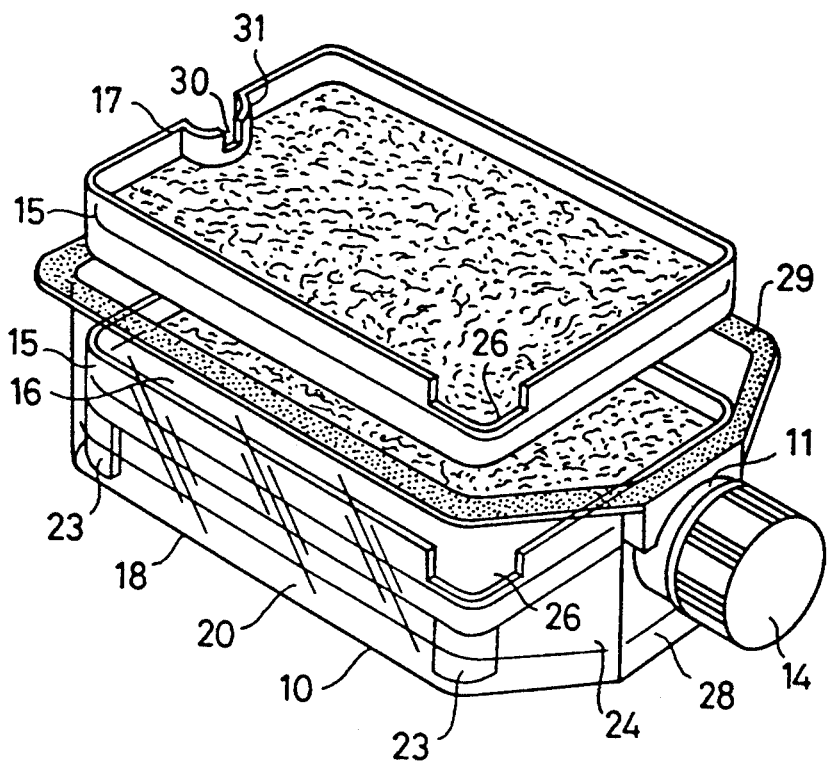

The embodiment shown in FIGS. 3 and 4 differs from that shown in FIGS. 1 and 2 in that the container top wall 19, which may be made from a flexible plastic film, is removably connected to a stiffer container main part 28. When the partition wall members 15 have been arranged within the upwardly open container main part 28 the top wall 19 may be sealingly and removably connected to a substantially planar flange portion 29 by heat sealing or by means of an adhesive.

It should be understood that the tear-off wall could alternatively be defined by weakening lines or score lines formed in a wall part of the outer container 10, for example in the top wall 19. Even when the top wall has not been provided with such score lines, the main part of the top wall 19 may be cut out by means of a suitable cutting tool so as to form an opening through which the partition wall members 15 may be taken out from the outer container 10.

In FIGS. 5-8 the interconnecting passage or tunnel, which is defined by aligned outer channels in the upstanding peripheral side walls 17 of the partition wall members 15, has a rectangular or square cross-sectional shape. The cultivating device or apparatus comprises two superposed partition wall members 15 defining three cultivating chambers within the container or flask 10. In order to prevent foaming liquid in any of the partition wall members to leak into a lower cultivating chamber or compartment, the upper free edge 32 (FIG. 8) of the lower partition wall member 15 is sealingly connected to the adjacent bottom surface of the upper partition wall member, for example by heat sealing or gluing. The partition wall members 15 are preferably sealingly interconnected along their total outline, except for the openings 26 and 30.

In order to reduce or eliminate leakage or foaming liquid from the upper partition wall member 15 into one of the lower chambers or compartments via the capillary space defined between the peripheral side wall 17 of the upper partition wall member and the adjacent inner surface of the container walls, the upper free edge 33 (FIGS. 7, 9 and 10) is spaced from the inner surface of the top wall 19, for example by means of spacer lugs 34 formed on the inner side surface of the top wall 19 at the corners thereof. The spacing of the upper free edge 33 of the peripheral wall 17 from the inner surface of the top wall 19 may, for example, be about 1-2 mm.

Alternatively or additionally, the upper free edge of the side wall 17 of the upper partition wall member may be provided with a layer 35 of a hydrophobic material as illustrated in FIG. 9 and/or the upper free edge 33 may be sharpened so as to define a sharp edge as illustrated in FIG. 10. As the free edge 33 of the upper partition wall member is spaced from the inner surface of the top wall 19 the tunnel 31 may interconnect the upper and lower cultivating chambers or compartments via its open ends, which means that no cut-out is needed in the tunnel walls at its upper end as shown in FIGS. 2 and 4. The intermediate cultivating chamber or compartment may, however, be in communication with the inner space of the tunnel 31 through a cut-out 30 in the tunnel wall at the upper edge of the lower partition wall member. This cut-out is preferably spaced inwardly from the plane of the adjacent peripheral wall 17 as best illustrated in FIG. 8.

As indicated by dotted lines in FIG. 8, each of the outer channels formed in the peripheral side walls 17 of the partition wall members 15 may be closed by an outer wall part 36. This means that the tunnel 31 is defined totally by wall parts of the partition wall members 15.

It should be understood that various changes and modifications of the embodiment described above with reference to the drawings could be made within the scope of the present invention. Thus, in the embodiments illustrated in FIGS. 1-4, the superposed partition wall members could be sealingly interconnected so as to form a unitary insert as explained in connection with FIGS. 5-8. Similarly, in FIGS. 1-4 the upper free edge of the upper partition wall member 15 may be spaced from the inner surface of the container top wall 19. Furthermore, the interconnecting passage or tunnel 31 shown in the drawings could be replaced by two or more such tunnels each having a smaller cross-sectional area. As an example, the interconnecting passage or passages could be defined in rib-like depressions formed in the flat end wall 21 of the container.

We claim:
1. A cell cultivating device comprising
an outer closable container having a substantially flat container bottom wall, a top wall, a substantially flat first end wall extending at substantially right angles to the flat container bottom wall, a second end wall, and opposite side walls interconnecting the top and container bottom walls and the end walls, one of said walls defining a closable filling opening therein,
an insert positioned within the outer container and including at least first and second interconnected partition wall members, each of the partition wall members including a flat chamber bottom wall extending substantially parallel with the flat container bottom wall and a peripheral wall surrounding the partition wall at its outer edge and extending therefrom toward the container top wall, each of said peripheral walls engaging with adjacent inner surface parts of the container walls, and said chamber bottom walls dividing an inner space defined by the outer container into superposed cultivating chambers,
passage means for mutually fluidly interconnecting all of the superposed cultivating chambers so that liquid introduced into the container via the closable filling opening may distribute itself in all of the interconnected chambers when the container is placed in an upright position in which it is supported by the flat first end wall, said passage means comprises an interconnecting passage defined adja- cent to an inner side surface part of the flat first end wall, each chamber communicating with the interconnecting passage through a connecting opening provided in the respective peripheral wall extending along only a fraction of the width of the first end wall being spaced from the bottom wall of the respective cultivating chamber.

2. A cell cultivating device according to claim 1, wherein the second partition wall member is supported by a free edge portion of the first partition wall member.

3. A cell cultivating device according to claim 1, wherein the chamber bottom wall of the first partition wall member is separated from the bottom wall of the container so as to define a cultivating chamber between the first partition wall member and the container bottom wall.

4. A cell cultivating device according to claim 1, wherein adjoining partition wall members are sealingly interconnected along at least a part of the peripheries of the partition wall members which are spaced apart along any non-interconnected peripheral parts.

5. A cell cultivating device according to claim 1, wherein the closable filling opening is defined in said second end wall of the container.

6. A cell cultivating device according to claim 1, wherein the interconnecting passage is a tunnel defined between said inner side surface part of the flat first end wall and an opposite outer surface part of the peripheral wall of each partition wall members.

7. A cell cultivating device according to claim 6, wherein said outer surface part of the peripheral wall defines a channel.

8. A cell cultivating device according to claim 6, wherein the tunnel defining the interconnecting passage has open ends positioned opposite to and spaced from the container bottom and top walls, respectively, of the outer container.

9. A cell cultivating device according to claim 1, wherein the interconnecting passage is a tunnel extending through and being defined totally by the peripheral wall of each partition wall member.

10. A cell cultivating device according to claim 1, wherein the interconnecting passage has a quadrangular cross-sectional shape.

11. A cell cultivating device according to claim 9, wherein the interconnecting passage has a substantially rectangular cross-sectional shape.

12. A cell cultivating device according to claim 1, wherein each connecting opening extends along less than ⅓ of the width of the first end wall of the container.

13. A cell cultivating device according to claim 12, wherein each connecting opening extends along less than ¼ of the width of the first end wall of the container.

14. A cell cultivating device according to claim 13, wherein the connecting opening extends along approximately 1/10 of the width of the first end wall of the container.

15. A cell cultivating device according to claim 1, wherein except for the interconnecting passage the peripheral wall of each partition wall member is in abutting engagement with adjacent inner surface parts of the flat first end wall and of adjacent parts of the opposite side walls of the outer container.

16. A cell cultivating device according to claim 1, wherein the free edge of the peripheral wall of the partition wall member positioned adjacent to the top wall of the container is spaced from said top wall.

17. A cell cultivating device according to claim 16, wherein said spacing is 1-2 mm.

18. A cell cultivating device according to claim 1, wherein the free edge of the peripheral wall of the partition wall member positioned adjacent to the top wall of the container defines a sharp edge.

19. A cell cultivating device according to claim 1, wherein the free edge of the peripheral wall of the partition wall member positioned adjacent to the top wall of the container is hydrophobic.

20. A cell cultivating device according to claim 1, wherein the outer container is made from two parts which have been sealingly interconnected after insertion of said insert therein.

21. A cell cultivating device according to claim 20, wherein the container comprises a tear-off wall part.

22. A cell cultivating device according to claim 21, wherein the tear-off wall part is one of said two parts.

23. A cell cultivating device according to claim 1, wherein the closable filling opening communicates with a manifold chamber defined within the outer container and being in communication with at least one of the cultivating chambers via an inlet opening provided in the peripheral wall of at least one of the partition wall members.

24. A cell cultivating device according to claim 1, wherein the outer container is a bottle or flask.

25. A cell cultivating device comprising an outer container, having a substantially flat container bottom wall, a container top wall, a substantially flat first end wall extending at substantially right angles to the flat container bottom wall, a second end wall, and opposite side walls interconnecting the container top and container bottom walls and the end walls, one of said walls defining a closable filling opening therein, at least two superposed partition wall members dividing an inner space of the outer container into superposed cultivating chambers, each partition wall member having a flat chamber bottom wall and a surrounding peripheral wall extending from the chamber bottom wall towards the top container wall and engaging with adjacent inner surface parts of the container walls, the chamber bottom walls, which are mutually spaced and spaced from the container top and container bottom walls, respectively, extending substantially parallel with the container bottom wall, and adjoining partition wall members having their peripheral walls sealingly interconnected along at least a major part of the peripheries of the partition wall members, the partition wall members being spaced apart along any non-interconnected parts by said peripheries, and liquid passage means for mutually and fluidly interconnecting all of the cultivating chambers so that liquid introduced into the container via the closable filling opening may distribute itself in all of the interconnected chambers when the container is placed in an upright position in which it is supported by the flat first end wall.

26. A cell cultivating device according to claim 25, wherein the closable filling opening is defined in said second end wall of the container.

27. A cell cultivating device according to claim 25, wherein a free edge of the peripheral wall of the partition wall member positioned adjacent to the top wall of the container is spaced from said top wall.

28. A cell cultivating device according to claim 25, wherein said spacing is 1-2 mm.

29. A cell cultivating device according to claim 25, wherein the free edge of the peripheral wall of the partition wall member positioned adjacent to the top wall of the container defines a sharp edge.

30. A cell cultivating device according to claim 25, wherein the free edge of the peripheral wall of the partition wall member positioned adjacent to the top all of the container is hydrophobic.

31. A cell cultivating device according to claim 25, wherein the partition wall members are interconnected to define an insert positioned within the outer container.

32. A cell cultivating device according to claim 31, wherein the outer container is made from two parts which have been sealingly interconnected after insertion of said insert therein.

33. A cell cultivating device according to claim 32, wherein the container comprises a tear-off wall part.

34. A cell cultivating device according to claim 32, wherein the tear-off wall part is one of said container parts.

35. A cell cultivating device according to claim 25, wherein the closable filling opening communicates with a manifold chamber defined within the outer container and being in communication with at least one of the cultivating chambers via an inlet opening provided in the peripheral wall of at least one of the partition wall members.

36. A cell cultivating device according to claim 25, wherein the container is a bottle or flask.

* * * * *

UNITED STATES PATENT AND TRADEMARK OFFICE
CERTIFICATE OF CORRECTION

PATENT NO. : 5,310,676
DATED : May 10, 1994
INVENTOR(S) : Johansson et al.

It is certified that error appears in the above-indentified patent and that said Letters Patent is hereby corrected as shown below:

Column 1, line 29, "o" should be --of--;

Column 3, line 2, "form" should be --from--;

Column 4, line 27, delete "cultivating" (second occurrence); and

Column 8, line 57, "be" should be --by--.

Signed and Sealed this

Twenty-second Day of November, 1994

Attest:

BRUCE LEHMAN

Attesting Officer     Commissioner of Patents and Trademarks